United States Patent
Ward et al.

(10) Patent No.: US 9,732,225 B2
(45) Date of Patent: *Aug. 15, 2017

(54) BENZOXAZINE RESINS

(71) Applicant: CYTEC TECHNOLOGY CORP., Wilmington, DE (US)

(72) Inventors: Steven Richard Ward, Buckley (GB); Paul Mark Cross, Dringhouses (GB); Robin Maskell, Phoenix, AZ (US)

(73) Assignee: CYTEC TECHNOLOGY CORP., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/985,550

(22) Filed: Dec. 31, 2015

(65) Prior Publication Data
US 2016/0115317 A1    Apr. 28, 2016

Related U.S. Application Data (62) Division of application No. 13/981,640, filed as application No. PCT/EP2012/050307 on Jan. 10, 2012, now Pat. No. 9,255,075.

(30) Foreign Application Priority Data

Jan. 25, 2011  (GB) .................................. 1101302.6

(51) Int. Cl.
  *C08L 79/04*    (2006.01)
  *C08L 81/06*    (2006.01)
  (Continued)

(52) U.S. Cl.
  CPC ............ *C08L 81/06* (2013.01); *C07D 265/16* (2013.01); *C08G 73/026* (2013.01);
  (Continued)

(58) Field of Classification Search
  CPC ...................... C08G 75/20–75/22; C08L 81/06
  See application file for complete search history.

(56) References Cited

U.S. PATENT DOCUMENTS

| | | |
|---|---|---|
| 4,607,091 A | 8/1986 | Schreiber |
| 4,806,267 A | 2/1989 | Culbertson et al. |

(Continued)

FOREIGN PATENT DOCUMENTS

| | | |
|---|---|---|
| WO | 95/31447 A1 | 11/1995 |
| WO | 2011/047929 A1 | 4/2011 |

OTHER PUBLICATIONS

Lin et al.: "Aromatic diamine-based benzoxazines and their high performance thermosets", Polymer, Elsevier Science Publichsers B.V., GB, vol. 49, No. 5, Jan. 11, 2008.
(Continued)

*Primary Examiner* — Robert C Boyle
*Assistant Examiner* — Stephen Rieth
(74) *Attorney, Agent, or Firm* — Thi Dang (57) ABSTRACT

A curable polymer composition containing: (A) a thermoset benzoxazine resin precursor component; (B) optionally, an aryl sulphone-containing benzoxazine component, and (C) a polyarylsulphone thermoplastic toughening agent, wherein in the absence of component (B), component (C) contains one or more benzoxazine pendant- and/or end-groups.

8 Claims, 2 Drawing Sheets

(51) Int. Cl.
  C08G 73/22   (2006.01)
  C08G 73/02   (2006.01)
  C08L 79/02   (2006.01)
  C07D 265/16  (2006.01)

(52) U.S. Cl.
  CPC ......... *C08G 73/0233* (2013.01); *C08G 73/22* (2013.01); *C08L 79/02* (2013.01); *C08L 79/04* (2013.01); *C08L 2205/03* (2013.01); *C08L 2205/08* (2013.01)

(56) References Cited

U.S. PATENT DOCUMENTS

| | | | |
|---|---|---|---|
| 5,021,484 | A | 6/1991 | Schreiber et al. |
| 5,200,452 | A | 4/1993 | Schreiber |
| 5,445,911 | A | 8/1995 | Russell et al. |
| 6,207,786 | B1 | 3/2001 | Ishida et al. |
| 7,517,925 | B2 | 4/2009 | Dershem et al. |
| 7,666,938 | B2 * | 2/2010 | Li .................. C08G 61/12 524/492 |
| 9,255,075 | B2 * | 2/2016 | Ward ............... C08G 73/0233 |
| 2008/0045688 | A1 | 2/2008 | Lin et al. |
| 2009/0299062 | A1 | 12/2009 | Eguchi et al. |

OTHER PUBLICATIONS

Agag T et al: "A new synthetic approach for difficult benzoxazines: Preparation and polymerization of 4, 4'-diaminodiphenyl sulfone-based benzoxazine monomer", Polymer, Elsevi, Polymer, 2009, vol. 50, pp. 5940-5944.

Sahin Ates et al: "Synthesis, characterization and thermally activated curing of polysulfones with benzoxazine end groups", Polymer, Elsevier Science Publishers B.V., GB, Polymer, 2011, vol. 52, pp. 1504-1509.

Rimdusit et al: "Development of new class of electronic packaging materials based on ternary system of benzoxazine, epoxy, and phenolic resin" Polymer, 41, 7941-49 (2000).

McGrath et al: "Synthesis and Characterization of Segmented Polyimide-Polyorganosiloxane Copolymers", Advances in Polym. Scl., vol. 140, Springer-Veriag, Berlin 61-105 (1999).

J. Jang et al.: "Performance Improvement of Rubber Modified Polybenzoxazine", J. Appl. Polym. Scl., 67, 1-10 (1998).

* cited by examiner

BENZOXAZINE RESINS

CROSS-REFERENCE TO RELATED APPLICATIONS

This application is a Divisional Application of U.S. application Ser. No. 13/981,640 filed Sep. 6, 2013, which is a national stage entry of the International Application No. PCT/EP2012/050307 filed Jan. 10, 2012, which claims benefit of priority from United Kingdom Application No. 1101302.6 filed Jan. 25, 2011, all of which are incorporated herein by reference.

FIELD OF THE INVENTION

The present invention relates to the preparation of benzoxazine-terminated sulfone-containing molecules, and their use as compatibilising agents for toughening agents in benzoxazine resins, as well as the use of benzoxazine-terminated sulfone-containing molecules as toughening agents in benzoxazine resins in their own right.

BACKGROUND

The use of benzoxazine compounds in the preparation of thermosetting resins offers a number of advantages, including their relatively long shelf-life, molecular design flexibility, low cost, high glass-transition temperature, high modulus, relatively low viscosities, flame retardancy, low moisture absorption and very low shrinkage. In addition, because their polymerisation is effected via a ring-opening mechanism (as shown for di-functional benzoxazines in scheme 1 below), the generation of troublesome condensation by-products can be avoided.

Scheme 1

WO-95/31447-A teaches the preparation of a number of benzoxazine compounds in solvent-less systems. Nevertheless, while benzoxazines have a number of advantages over other thermosetting matrices, their main disadvantage is that they are generally very brittle, and there are no commercially available pure benzoxazine matrices suitable for use in high performance composites. Typically, benzoxazines have a very poor compatibility with commonly used thermoplastic toughening-agents, and this incompatibility leads either to difficulty in dissolving the thermoplastic material into the base resin during mixing or to the gross phase separation of the thermoplastic during cure. Toughening of benzoxazine systems has been limited to the use of rubbers, modified benzoxazine monomers and low performance thermoplastics but these also reduce the beneficial properties of benzoxazines, most notably the modulus and high glass transition temperature.

Several benzoxazine hybrid systems are commercially available (such as the benzoxazine-epoxy hybrid systems available as Araldite® MT resins) but the addition of the co-reactant (epoxy) can negate some of the advantages of benzoxazines. There is currently no available benzoxazine system that retains all of the beneficial properties of neat benzoxazines but that exhibits a toughness suitable for high performance applications.

SUMMARY

It is an object of this invention to solve one or more of the afore-mentioned problems. In particular, it is an object of this invention to provide a benzoxazine thermoset resin which exhibits high toughness and excellent modulus. It is a further object of this invention to provide a benzoxazine thermoset resin which exhibits high toughness and excellent modulus wherein the thermoset resin component consists of benzoxazine resin(s).

According to the present invention, there is provided a curable polymer composition comprising:
(A) a thermoset benzoxazine resin precursor component;
(B) optionally an arylsulphone-containing benzoxazine component, and
(C) a polyarylsulphone thermoplastic toughening agent component,
wherein in the absence of component (B), said component (C) comprises one or more benzoxazine pendant- and/or end-groups.

According to a further aspect of the present invention, there is provided a thermoset resin composition derived from reaction of a composition comprising the following components, optionally in the presence of a curing agent:
(A) a thermoset benzoxazine resin precursor component;
(B) optionally an arylsulphone-containing benzoxazine component; and
(C) a polyarylsulphone thermoplastic toughening agent component,
wherein in the absence of component (B), said component (C) comprises one or more benzoxazine pendant- and/or end-groups.

DETAILED DESCRIPTION

As used herein, a "curable polymer composition" refers to a composition prior to curing and a "thermoset resin composition" refers to a post-cured composition.

Component (B) is a relatively low molecular weight monomeric or oligomeric arylsulphone-containing benzoxazine compound, which interacts with the thermosetting benzoxazine resin precursor component (A) and compatibilises the polyarylsulphone thermoplastic component (C) to the matrix resin. It is believed that component (B) acts to change the solubility parameters of the base resin, allowing the morphology to be controlled.

In a first embodiment, component (C) is not functionalised with benzoxazine end-groups, and component (B) is mandatory. The non-functionalised polyarylsulphone thermoplastic toughening agent (i.e. without benzoxazine end-groups) in this embodiment is referred to hereinafter as component (C-i).

In a second embodiment, component (C) is functionalised with one or more benzoxazine end-groups and performs both toughening and compatibilising functions. The formation of benzoxazine groups on the end(s) of a polyarylsulphone thermoplastic toughening agent, allowing the thermoplastic to react into, and compatibilise with, the thermosetting matrix resin (A). The functionalised polyarylsulphone thermoplastic toughening agent (i.e. comprising benzoxazine end-groups) in this embodiment is referred to hereinafter as component (C-ii). In this embodiment, the component (B) may or may not be present, but it is preferred that component (B) is present in those embodiments wherein the number average molecular weight of component (C) is about 7000 or above, particularly about 9000 or above.

The present invention allows benzoxazine thermosetting resins to be used in high-performance composites, for instance in demanding aerospace applications, by compatibilising thermoplastic toughening agents with the benzoxazine resin, thereby providing toughening without significantly reducing the modulus or glass transition temperature of the benzoxazine resin.

The Thermoset Benzoxazine Resin Precursor Component (A)

The thermoset benzoxazine resin precursor component comprises one or more polymerisable benzoxazine compound(s). The polymerisable benzoxazine compound may be mono-functional, in which there is a single benzoxazine moiety in the compound, but is preferably at least di-functional and contains at least two benzoxazine moieties in the compound, enabling the formation of cross-links. Tri-functional precursors are also encompassed within the scope of the invention. In a preferred embodiment, the precursor is di-functional and contains two benzoxazine moieties. The precursor component may comprise a blend of one or more mono-functional polymerisable benzoxazine compounds and/or one or more di-functional polymerisable benzoxazine compounds and/or one or more tri-functional polymerisable benzoxazine compound(s) and/or one or more polymerisable benzoxazine compounds with greater functionality. In a further preferred embodiment, the precursor component comprises a blend of one or more mono-functional polymerisable benzoxazine compounds with one or more di-functional polymerisable benzoxazine compounds.

Preferably, the precursor is selected from compounds of formula (I) below:

wherein:
$Z^1$ is selected from a direct bond, —C($R^3$)($R^4$)—, —C($R^3$)(aryl)-, —C(O)—, —S—, —O—, —S(O)—, —S(O)$_2$—, a divalent heterocycle and —[C($R^3$)($R^4$)]$_x$-arylene-[C($R^5$)($R^6$)]$_y$—, or the two benzyl rings of the benzoxazine moieties may be fused; and
$R^1$ and $R^2$ are independently selected from alkyl (preferably $C_{1-8}$ alkyl), cycloalkyl (preferably $C_{5-7}$ cycloalkyl, preferably $C_6$ cycloalkyl) and aryl, wherein the cycloalkyl and aryl groups are optionally substituted, for instance by $C_{1-8}$ alkyl, halogen and amine groups, and preferably by $C_{1-8}$ alkyl, and where substituted, one or more substituent groups (preferably one substituent group) may be present on the or each cycloalkyl and aryl group;
$R^3$, $R^4$, $R^5$ and $R^6$ are independently selected from H, $C_{1-8}$ alkyl (preferably $C_{1-4}$ alkyl, and preferably methyl), and halogenated alkyl (wherein the halogen is typically chlorine or fluorine (preferably fluorine) and wherein the halogenated alkyl is preferably $CF_3$); and
x and y are independently 0 or 1.

In one embodiment, $Z^1$ is selected from a direct bond, —C($R^3$)($R^4$)—, —C($R^3$)(aryl)-, —C(O)—, —S—, —O—, a divalent heterocycle and —[C($R^3$)($R^4$)]$_x$-arylene-[C($R^5$)($R^6$)]$_y$—, or the two benzyl rings of the benzoxazine moieties may be fused.

Where $Z^1$ is selected from a divalent heterocycle, it is preferably 3,3-isobenzofuran-1(3H)-one, i.e. wherein the compound of formula (I) is derived from phenolphthalein.

Where $Z^1$ is selected from —[C($R^3$)($R^4$)]$_x$-arylene-[C($R^5$)($R^6$)]$_y$—, then the chain linking the two benzoxazine groups may further comprise, or be optionally interrupted by, one or more arylene group(s) and/or one or more —C($R^7$)($R^8$)—group(s) (where $R^7$ and $R^8$ are independently selected from the groups defined hereinabove for $R^3$), provided that the or each substituted or unsubstituted methylene group is not adjacent to another substituted or unsubstituted methylene group.

In a preferred embodiment, said arylene group is phenylene. In one embodiment, the groups attached to the phenylene group may configured in para- or meta-positions relative to each other.

The group $Z_1$ may be linear or non-linear, and is typically linear.

The group $Z_1$ is preferably bound to the benzyl group of each of the benzoxazine moieties at the para-position relative to the oxygen atom of the benzoxazine moieties, as shown in formula (I), and this is the preferred isomeric configuration. However, the group $Z_1$ may also be attached at either of the meta-positions or the ortho-position, in one or both of the benzyl group(s) in the bis-benzoxazine compound. Thus, the group $Z_1$ may be attached to the benzyl rings in a para/para; para/meta; para/ortho, meta/meta or ortho/meta configuration. In one embodiment, the thermoset benzoxazine resin component (A) comprises a mixture of isomers, preferably wherein the major portion of the mixture is the para/para isomer shown in formula (I), and preferably this is present in at least 75 mol %, preferably at least 90 mol %, and preferably at least 99 mol %, of the total isomeric mixture.

In a preferred embodiment, said aryl group is phenyl.

In a preferred embodiment, the precursor is selected from compounds wherein $Z^1$ is selected from —C(CH$_3$)$_2$—, —CH$_2$— and 3,3-isobenzofuran-1(3H)-one, i.e. benzoxazine derivatives of bisphenol A, bisphenol F and phenolphthalein.

In a preferred embodiment, the precursor is selected from compounds wherein $R^1$ and $R^2$ are independently selected from aryl, preferably phenyl. In one embodiment, the or each aryl group may be substituted, preferably wherein the substituent(s) are selected from $C_{1-8}$ alkyl, and preferably wherein there is a single substituent present on the or each aryl group. Preferably $R^1$ and $R^2$ are independently selected from unsubstituted aryl, preferably unsubstituted phenyl.

Such benzoxazine resin precursor compounds can be synthesised by the reaction between a bisphenol, formaldehyde and an amine using conventional techniques well-known in the art, for instance by the methods disclosed in WO-95/31447-A.

Suitable mono-functional polymerisable benzoxazine compound(s) may be derived from the reaction product of a phenol, an amine and formaldehyde wherein the substituents on the amine are selected from those define for $R^1$ hereinabove.

The benzyl ring in the or each benzoxazine group of the polymerisable benzoxazine compounds defined herein may be independently substituted at any of the three available positions of each ring, and typically any optional substituent is present at the position ortho to the position of attachment of the $Z^1$ group. Preferably, however, the benzyl ring remain unsubstituted.

In a further embodiment, the polymerisable benzoxazine compound is selected from any of the bis-benzoxazine compounds disclosed in US-2008/0045688-A1 and US-2009/0054614-A1, the disclosures of which are incorporated herein by reference. In a further embodiment, the polymerisable benzoxazine compound is selected from any of the tris-benzoxazine compounds disclosed in US-2008/0045688-A1, the disclosure of which is incorporated herein by reference.

The Thermoplastic Toughening Agent Component (C)

The thermoplastic toughening agent (C) comprises one or more polyarylsulphone(s) comprising ether-linked repeating units, optionally further comprising thioether-linked repeating units, the units being selected from:

—[ArSO$_2$Ar]$_n$— and optionally from:

—[Ar]$_a$— wherein:
Ar is phenylene;
n=1 to 2 and can be fractional;
a=1 to 3 and can be fractional and when a exceeds 1, said phenylene groups are linked linearly through a single chemical bond or a divalent group other than —SO$_2$— (preferably wherein the divalent group is a group —C(R$^9$)$_2$— wherein each R$^9$ may be the same or different and selected from H and $C_{1-8}$ alkyl (particularly methyl)), or are fused together, provided that the repeating unit —[ArSO$_2$Ar]$_n$— is always present in the polyarylsulphone in such a proportion that on average at least two of said —[ArSO$_2$Ar]$_n$— units are in sequence in each polymer chain present,
and wherein the polyarylsulphone has one or more reactive pendant and/or end group(s).

By "fractional" reference is made to the average value for a given polymer chain containing units having various values of n or a.

In one embodiment, the phenylene groups in the polyarylsulphones are linked through a single bond.

The phenylene groups in the polyarylsulphones may be substituted by one or more substituent groups (R), each independently selected from $C_{1-8}$ branched or straight chain aliphatic saturated or unsaturated aliphatic groups or moieties optionally comprising one or more heteroatoms selected from O, S, N, or halo (for example Cl or F); and groups providing active hydrogen especially OH, NH$_2$, NHR$^a$ or —SH, where R$^a$ is a hydrocarbon group containing up to eight carbon atoms, or providing other cross-linking activity especially benzoxazine, epoxy, (meth)acrylate, cyanate, isocyanate, acetylene or ethylene, as in vinyl, allyl or maleimide, anhydride, oxazoline and monomers containing unsaturation.

Preferably, the phenylene groups are meta- or para- (preferably para). A mixture of conformations (particularly meta- and para-conformations) may be present along the polymer backbone.

Preferably the polyarylsulphone comprises a combination of —[ArSO$_2$Ar]$_n$— and —[Ar]$_a$— repeating units, linked by ether and/or thio-ether linkages, preferably by ether linkages. Thus, preferably the polyarylsulphone comprises a combination of polyethersulphone (PES) and polyetherethersulphone (PEES) ether-linked repeating units.

The relative proportions of —[ArSO$_2$Ar]$_n$— and —[Ar]$_a$— repeating units is such that on average at least two —[ArSO$_2$Ar]$_n$— repeating units are in immediate mutual succession in each polymer chain present, and the ratio of —[ArSO$_2$Ar]$_n$— units to —[Ar]$_a$— units is preferably in the range 1:99 to 99:1, more preferably 10:90 to 90:10. Typically, the ratio [ArSO$_2$Ar]$_n$:[Ar]$_a$ is in the range 75:25 to 50:50.

In one embodiment, the preferred repeating units in the polyarylsulphones are:

—X—Ar—SO$_2$—Ar—X—Ar—SO$_2$—Ar— (referred to herein as a "PES unit")    (I):

and

—X—(Ar)$_a$—X—Ar—SO$_2$—Ar— (referred to herein as a "PEES unit")    (II):

wherein:
X is O or S (preferably O) and may differ from unit to unit; and
the ratio of units I:II is preferably in the range of from 10:90 to 80:20, more preferably in the range of from 10:90 to 55:45, more preferably in the range of from 25:75 to 50:50, and in one embodiment, the ratio I:II is in the range of from 20:80 to 70:30, more preferably in the range of from 30:70 to 70:30, most preferably in the range of from 35:65 to 65:35.

The preferred relative proportions of the repeating units of the polyarylsulphone may be expressed in terms of the weight percent SO$_2$ content, defined as 100 times (weight of SO$_2$)/(weight of average repeat unit). The preferred SO$_2$ content is at least 22, preferably 23 to 25%. When a=1 this corresponds to PES/PEES ratio of at least 20:80, preferably in the range 35:65 to 65:35.

The flow temperature of polyetherethersulphone is generally less than that of a corresponding Mn polyethersulphone, but both possess similar mechanical properties. Accordingly the ratio may be determined, by determining values for a and n above.

U.S. Pat. No. 6,437,080 discloses processes for obtaining such compositions from their monomer precursors in a manner to isolate the monomer precursors in selected molecular weight as desired, and those disclosures are incorporated herein by reference.

The above proportions refer only to the units mentioned. In addition to such units the polyarylsulphone may contain up to 50% molar, preferably up to 25% molar, of other repeating units: the preferred $SO_2$ content ranges then apply to the whole polymer. Such units may be for example of the formula:

in which L is a direct link, oxygen, sulphur, —CO— or a divalent group (preferably a divalent hydrocarbon radical, preferably wherein the divalent group is a group —$C(R^{12})_2$— wherein each IC may be the same or different and selected from H and $C_{1-8}$ alkyl (particularly methyl)).

When the polyarylsulphone is the product of nucleophilic synthesis, its units may have been derived for example from one or more bisphenols and/or corresponding bis-thiols or phenol-thiols selected from hydroquinone, 4,4'-dihydroxybiphenyl, resorcinol, dihydroxynaphthalene (2,6 and other isomers), 4,4'-dihydroxybenzophenone, 2,2'-di(4-hydroxyphenyl)propane and -methane. If a bis-thiol is used, it may be formed in situ, that is, a dihalide may be reacted with an alkali sulphide or polysulphide or thiosulphate.

Other examples of such additional units are of the formula:

in which Q and Q', which may be the same or different, are CO or $SO_2$; Ar' is a divalent aromatic radical; and p is 0, 1, 2, or 3, provided that p is not zero where Q is $SO_2$. Ar' is preferably at least one divalent aromatic radical selected from phenylene, biphenylene or terphenylene. Particular units have the formula:

where q is 1, 2 or 3. When the polymer is the product of nucleophilic synthesis, such units may have been derived from one or more dihalides, for example selected from 4,4'-dihalobenzophenone, 4,4'bis(4-chlorophenylsulphonyl) biphenyl, 1,4,bis(4-halobenzoyl)benzene and 4,4'-bis(4-halobenzoyl)biphenyl. They may of course have been derived partly from the corresponding bisphenols.

The polyarylsulphone may be the product of nucleophilic synthesis from halophenols and/or halothiophenols. In any nucleophilic synthesis the halogen if chlorine or bromine may be activated by the presence of a copper catalyst. Such activation is often unnecessary if the halogen is activated by an electron withdrawing group. In any event, fluoride is usually more active than chloride. Any nucleophilic synthesis of the polyarylsulphone is carried out preferably in the presence of one or more alkali metal salts, such as KOH, NaOH or $K_2CO_3$ in up to 10% molar excess over the stoichiometric.

As noted above, the polyarylsulphone contains one or more reactive pendant and/or end-group(s), and in a preferred embodiment the polyarylsulphone contains two such reactive pendant and/or end-group(s). In one embodiment, the polyarylsulphone comprises one such reactive pendant- and/or end-group. Reactive end-groups may be obtained by a reaction of monomers or by subsequent conversion of product polymers prior to, or subsequently to, isolation. Preferably, the reactive pendant- and/or end-groups are groups providing active hydrogen, particularly OH, $NH_2$, $NHR^b$ or —SH (where $R^b$ is a hydrocarbon group containing up to eight carbon atoms), or are groups providing other cross-linking activity, particularly benzoxazine, epoxy, (meth)acrylate, cyanate, isocyanate, acetylene or ethylene, as in vinyl, allyl or maleimide, anhydride, oxazaline and monomers containing saturation. In one embodiment, the reactive pendant- and/or end-groups are of formula -A'-Y wherein A' is a bond or a divalent hydrocarbon group, preferably aromatic, preferably phenyl. Examples of Y are groups providing active hydrogen, particularly OH, $NH_2$, $NHR^b$ or —SH (where $R^b$ is a hydrocarbon group containing up to eight carbon atoms), or groups providing other cross-linking activity, particularly benzoxazine, epoxy, (meth) acrylate, cyanate, isocyanate, acetylene or ethylene, as in vinyl, allyl or maleimide, anhydride, oxazaline and monomers containing saturation. The groups providing other cross-linking activity may be bound to the Ar groups of the polyarylsulphone via a direct bond, or via an ether, thioether, sulphone, —CO— or divalent hydrocarbon radical linkage as described hereinabove, most typically via an ether, thio-ether or sulphone linkage. In a further embodiment, the end-groups, or more typically only a proportion thereof, may be selected from halo groups (particularly chloro). Component (C) may comprise a mixture of polyarylsulphones having differing end-groups. In one embodiment, where the polyarylsulphones of component (C) comprise a plurality of end-groups, at least 50 mol %, preferably at least 60 mol %, preferably at least 70 mol %, preferably at least 80 mol %, and preferably at least 85 mol % of the end-groups will be of one type.

In component (C-i), the reactive pendant- and/or end-group(s) is/are preferably selected from groups providing active hydrogen, particularly $NH_2$. Preferably, the polyarylsulphone comprises two such groups. In one embodiment, the polyarylsulphone comprises one such reactive pendant- and/or end-group.

In component (C-ii), the polyarylsulphone comprises at least one reactive pendant- and/or end-group selected from benzoxazine, and preferably two such groups, which is/are preferably situated at an or each end of the polymer backbone. Thus, in component (C-ii), the polyarylsulphone is typically terminated by benzoxazine end-groups. Other reactive pendant- and/or end-group(s) selected from the list hereinabove may also be present. In one embodiment, the polyarylsulphone comprises one such reactive pendant- and/or end-group.

The introduction of benzoxazine pendant- and/or end-groups may be achieved via the conventional reaction between an alcohol, an amine and formaldehyde. Thus, the benzoxazine group of component (C-ii) may be derived from an amine-terminated polyarylsulphone or an alcohol-terminated polyarylsulphone. A benzoxazine end-group of component (C-ii) derived from an amine-terminated polyarylsulphone is bound to the Ar groups of the polyarylsulphone via the N atom of the benzoxazine. A benzoxazine end-group of component (C-ii) derived from an alcohol-terminated polyarylsulphone is bound to the polymer backbone via a ring carbon atom of the benzyl ring of the benzoxazine, and may be bound to an O, S, $SO_2$ or other linkage as described herein, or to an Ar group.

The number average molecular weight of the polyarylsulphone is suitably in the range 2000 to 60000. Preferably, the molecular weight of polyarylsulphones suitable for use in the present invention is in the range of from about 2,000 to about 30,000, preferably from about 5,000 to about 15,000, preferably from about 7,000 to about 13,000, and in one embodiment from about 9,000 to about 12,000. In a further embodiment, the number average molecular weight is from 9000 to 25000 (preferably 11000 to 25000). In an alternative embodiment, the number average molecular weight is in the range of 3000 to 11000 (preferably 3000 to 9000). Such polyarylsulphones increases toughness structurally as well as by chemical interaction, when compared with the thermoset resin alone, by providing zones of the tough thermoplast between cross-linked thermoset zones. Where the number average molecular weight of a functionalised polyarylsulphone thermoplastic toughening agent component (C-ii) (i.e. comprising benzoxazine end-groups) is at least 7,000, and particularly at least 9,000, it is preferred that component (B) is present in the composition. Where the number average molecular weight of component (C-ii) is in the range of from 2,000 to about 9,000, particularly in the range of from 2,000 to about 7,000, component (B) is optionally present.

The synthesis of compounds according to component (C) is further described in US-2004/0044141 and U.S. Pat. No. 6,437,080, and those disclosures are incorporated herein by reference.

The Arylsulphone-Containing Benzoxazine Component (B)

The arylsulphone-containing benzoxazine component (B) comprises one or more arylsulphone-containing benzoxazine compounds. In a preferred embodiment, the arylsulphone-containing benzoxazine component (B) comprises one or more compounds selected from compounds of general formula (II):

(II)

wherein $Z^2$ comprises one or more arylsulphone unit(s), $-[Ar-SO_2-Ar]_n-$, and optionally further comprises one or more arylene unit(s) $-[Ar]_a-$, wherein said arylsulphone unit(s) and arylene unit(s) are linked by ether linkages ($-O-$) and/or thio-ether linkages ($-S-$), preferably by ether linkages and optionally also by thio-ether linkages, and preferably by ether linkages alone;

wherein Ar is phenylene;

n=1 to 2 and can be fractional;

a=1 to 3 and can be fractional and when a exceeds 1, said phenylene groups are linked linearly through a single chemical bond or a divalent group other than $-SO_2-$ (preferably wherein the divalent group is a group $-C(R^9)_2-$ wherein each $R^9$ may be the same or different and selected from H and $C_{1-8}$ alkyl (particularly methyl)), or are fused together; and wherein $R^{10}$ and $R^{11}$ are independently selected from H, alkyl (preferably $C_{1-8}$ alkyl), cycloalkyl (preferably $C_{5-7}$ cycloalkyl, preferably $C_6$ cycloalkyl) and aryl, wherein the cycloalkyl and aryl groups are optionally substituted, for instance by $C_{1-8}$ alkyl, halogen and amine groups, and preferably by $C_{1-8}$ alkyl, The group Ar in formula (II) may be substituted or unsubstituted, but is preferably unsubstituted. Where substituted, one or more substituent group(s) may be present, and selected from, for instance, from alkyl (preferably $C_{1-4}$ alkyl), unsaturated hydrocarbyl and halogen groups, and preferably from $C_{1-4}$ alkyl.

Preferably, the or each phenylene group is meta- or para- (and in one embodiment is para). A mixture of conformations (particularly meta- and para-conformations) may be present.

The Ar group in formula (II) is selected independently from the Ar group in component (C).

Some examples of compounds according to formula (II) are:

(II-a)

4,4'-DDS based benzoxazine (II-b)

3,3'-DDS based benzoxazine (II-c)

M-ESEDA based benzoxazine

In a further embodiment, the arylsulphone-containing benzoxazine component (B) comprises one or more compounds of general formula (II) wherein $R^{10}$ and $R^{11}$ are hydrogen, and wherein the benzyl ring of the benzoxazine group is further substituted at one or more of the available positions, particularly the 3- or 5-positions relative to the oxygen atom, by substituent group(s) independently selected from alkyl, cycloalkyl and aryl, as described hereinabove for $R^{10}$ and $R^{11}$.

In a further embodiment, the arylsulphone-containing benzoxazine component (B) comprises one or more compounds of general formula (II) wherein $R^{10}$ and $R^{11}$ are independently selected from alkyl, cycloalkyl and aryl, and wherein the benzyl ring of the benzoxazine group is further substituted at one or more of the available positions, particularly the 3- or 5-positions relative to the oxygen atom, by substituent group(s) independently selected from alkyl, cycloalkyl and aryl, as described hereinabove for $R^{10}$ and $R^{11}$.

Preferably, the $R^{10}$ and $R^{11}$ groups will be the same on each benzyl ring of the benzoxazine groups, and/or the location and identity of any additional substituent groups will be the same on each benzyl ring of the benzoxazine groups.

In an alternative embodiment, the arylsulphone-containing benzoxazine component (B) comprises one or more compounds selected from compounds of general formula (III):

(III)

wherein $R^{10}$ and $R^{11}$ are as defined for formula (II) but selected independently therefrom and $Z^3$ is selected from the group consisting of $SO_2$ and $Z^2$ as defined for formula (II) but selected independently therefrom.

The arylsulphone-containing benzoxazine component (B) may comprise a blend of one or more compounds of formula (II) and one or more compounds of formula (III).

The number average molecular weight of compounds suitable for use as component (B) is typically up to about 2000.

The benzoxazine-terminated compounds can be manufactured according to known methods, for instance the method disclosed in WO-95/31447-A. In general terms, a mixture of the phenol and amine compounds (in either stoichiometric ratios or in ratios with large excesses, depending on the reactivity of the components and their physical form) are heated at a temperature between about 80 and 130° C. for between about 30 minutes and 4 hours. Molten product is allowed to cool slightly, and then poured warm into stirring diethylether. The product may be recovered and purified by Soxhlet extraction in diethylether for 1-2 days, washed (e.g. with 0.1M NaOH solution at 70° C. for 30 minutes and then with water) and dried in vacuo.

Thermosetting Composition and Applications Therefor

The thermoset benzoxazine resin precursor component (A) is reacted with component (C), optionally in the presence of component (B), as described hereinabove, and optionally in the presence of a curing agent and/or catalyst, in relative amounts effective to provide a thermoset resin composition.

When used, the weight proportion of the arylsulphone-containing benzoxazine component (B) is typically present at no more than about 70% by weight, typically no more than about 60% by weight, typically no more than about 55% by weight, and preferably at least about 5% by weight, preferably at least about 8% by weight preferably at least about 10% by weight, preferably at least about 15% by weight, preferably at least about 20% by weight, preferably at least about 25% by weight, preferably at least about 30% by weight, preferably at least about 35% by weight, and preferably in the range of from about 15 to about 70%, more preferably from about 20 to about 60%, and especially from about 30 to about 55% by weight of the total weight of components (A), (B) and (C) in the composition. When component (A) is used in the presence of component (B), the identity of components (A) and (B) are different.

The weight proportion of the thermoplastic polyarylsulphone toughening agent (component (C)) is typically in the range of from about 5 to about 70%, more preferably from about 5 to about 50%, more preferably from about 5 to about 40%, and especially from about 5 to about 20% by weight of the total weight of components (A), (B) and (C) in the composition.

In the first embodiment of the invention, the arylsulphone-containing benzoxazine component (B) is preferably present in the range of from about 5 to about 70% by weight, preferably at least 10% by weight, preferably at least about 15% by weight, and otherwise as described hereinabove for the general and preferred ranges for component (B), and the thermoplastic polyarylsulphone component (C-i) is present in the range of from about 5% to about 70% by weight and otherwise as described hereinabove for the general and preferred ranges for component (C). The percentages are percentages by weight of the component relative to the total weight of components (A), (B) and (C) in the composition.

In the second embodiment of the invention, the benzoxazine-terminated thermoplastic polyarylsulphone component (C-ii) is typically present at no more than about 50% by weight and otherwise as described hereinabove for the general and preferred ranges for component (C). The polyarylsulphone-containing benzoxazine component (B) is optionally present in the amounts described hereinabove.

The curable polymer compositions of the invention are thermally curable. The addition of curing agents and/or catalysts is optional, but the use of such and may increase the cure rate and/or reduce the cure temperatures, if desired. In a preferred embodiment, the curable polymer compositions described hereinabove are thermally cured without the use of curing agents or catalysts.

In one embodiment, the composition further comprises one or more reactive diluent(s), for example thermoset polymer precursors, which may be useful as a processing aid for the benzoxazine resin systems described hereinabove. Thermoset resins may be selected from the group consisting of an epoxy resin, an addition-polymerisation resin (especially a bis-maleimide resin), a formaldehyde condensate resin (especially a formaldehyde-phenol resin), a cyanate resin, an isocyanate resin, a phenolic resin and mixtures of two or more thereof. Preferably the thermoset polymers are epoxy, phenolic or cyanate ester resins, particularly epoxy and phenolic resins, and particularly epoxy resins. An epoxy resin is preferably an epoxy resin derived from the mono or poly-glycidyl derivative of one or more of the group of compounds consisting of aromatic diamines, aromatic monoprimary amines, aminophenols, polyhydric phenols, polyhydric alcohols, polycarboxylic acids and the like, or a mixture thereof. Examples of addition-polymerisation resins are acrylics, vinyls, bis-maleimides, and unsaturated polyesters. Examples of formaldehyde condensate resins are urea, melamine and phenols. Where present, the thermoset resin in the composition comprises at least one epoxy, cyanate ester or phenolic resin precursor, which is liquid at ambient temperature, for example as disclosed in EP-A-0311349, EP-A-0365168, EP-A-0486197 or in U.S. Pat. No. 6,013,730.

An epoxy resin may be selected from N,N,N',N'-tetraglycidyl diamino diphenylmethane (e.g. grades MY 9663, MY 720 or MY 721; Ciba-Geigy); N,N,N',N'-tetraglycidyl-bis (4-aminophenyl)-1,4-diiso-propylbenzene (e.g. EPON 1071; Shell Chemical Co.); N,N,N',N'-tetraclycidyl-bis(4-amino-3,5-dimethylphenyl)-1,4-diisopropylbenzene, (e.g. EPON 1072; Shell Chemical Co.); triglycidyl ethers of p-aminophenol (e.g. MY 0510; Ciba-Geigy); diglycidyl ethers of bisphenol A based materials such as 2,2-bis(4,4'-dihydroxy phenyl)propane (e.g. DE R 661 (Dow), or Epikote 828 (Shell)), and Novolak resins preferably of viscosity 8-20 Pa s at 25° C.; glycidyl ethers of phenol Novolak resins (e.g. DEN 431 or DEN 438; Dow); diglycidyl 1,2-phthalate (e.g. GLY CEL A-100); diglycidyl derivative of dihydroxy diphenyl methane (Bisphenol F) (e.g. PY 306; Ciba Geigy). Other epoxy resin precursors include cycloaliphatics such as 3',4'-epoxycyclohexyl-3,4-epoxycyclohexane carboxylate (e.g. CY 179; Ciba Geigy) and those in the "Bakelite" range of Union Carbide Corporation.

A cyanate ester resin may be selected from one or more compounds of the central formula $NCOAr(Y_xAr_m)_qOCN$ and oligomers and/or polycyanate esters and combinations thereof wherein Ar is a single or fused aromatic or substituted aromatics and combinations thereof and therebetween nucleus linked in the ortho, meta and/or para position and x=0 to 2 and m and q=0 to 5 independently. The Y is a linking unit selected from the group consisting of oxygen, carbonyl, sulphur, sulphur oxides, chemical bond, aromatic linked in ortho, meta and/or para positions and/or $CR_1R_2$ wherein $R_1$ and $R_2$ are hydrogen, halogenated alkanes, such as the fluorinated alkanes and/or substituted aromatics and/or hydrocarbon units wherein said hydrocarbon units are singularly or multiply linked and consist of up to 20 carbon atoms for each $R_1$ and/or $R_2$ and $P(R_3R_4R'_4R_5)$ wherein $R_3$ is alkyl, aryl, alkoxy or hydroxy, $R'_4$ may be equal to $R_4$ and a singly linked oxygen or chemical bond and $R_5$ is doubly linked oxygen or chemical bond or $Si(R_3R_4R'_4R_6)$ wherein $R_3$ and $R_4$, $R'_4$ are defined as in $P(R_3R_4R'_4R_5)$ above and $R_5$ is defined similar to $R_3$ above. Optionally, the thermoset can consist essentially of cyanate esters of phenol/formaldehyde derived Novolaks or dicyclopentadiene derivatives thereof, an example of which is XU71787 sold by the Dow Chemical Company. It will be appreciated that the definitions of the R groups in the cyanate resins described in this paragraph are entirely distinct from the definitions of the R groups in components A and formula (I) of the present invention.

A phenolic resin may be selected from any aldehyde condensate resins derived from aldehydes such as methanal, ethanal, benzaldehyde or furfuraldehyde and phenols such as phenol, cresols, dihydric phenols, chlorphenols and $C_{1-9}$ alkyl phenols, such as phenol, 3- and 4-cresol (1-methyl, 3- and 4-hydroxy benzene), catechol (2-hydroxy phenol), resorcinol (1,3-dihydroxy benzene) and quinol (1,4-dihydroxy benzene). Preferred phenolic resins comprise cresol and novolak phenols.

A curing agent is preferred in those embodiments of the invention which comprise a reactive diluent. The curing agent is suitably selected from known curing agents, for example as disclosed in EP-A-0311349, EP-A-0486197, EP-A-0365168 or in U.S. Pat. No. 6,013,730, which are incorporated herein by reference, such as an amino compound having a molecular weight up to 500 per amino group, for example an aromatic amine or a guanidine derivative. Particular examples are 3,3'- and 4-,4'-diaminodiphenylsulphone (DDS); methylenedianiline; bis(4-amino-3,5-dimethylphenyl)-1,4-diisopropylbenzene (available as EPON 1062 from Shell Chemical Co.); bis(4-aminophenyl)-1,4-diisopropylbenzene (available as EPON 1061 from Shell Chemical Co.); 4-chlorophenyl-N,N-dimethyl-urea (e.g. Monuron); 3,4-dichlorophenyl-N,N-dimethyl-urea (e.g. Diuron™) and dicyanodiamide (Amicure™ CG 1200; Pacific Anchor Chemical). Bisphenol chain extenders, such as bisphenol-S or thiodiphenol, are particularly useful as curing agents for epoxy resins.

The curable polymer composition may comprise a curing agent and catalyst, for instance as disclosed in U.S. Pat. No. 6,265,491, the contents of which are incorporated herein by reference. Alternative catalysts may also be used, typically a Lewis acid or base, as is conventional in the art.

Where reactive diluents are used as described above, then the reactive diluent is typically present at about 20-40% by weight of the weight of component (A) in the composition, and the curing agent is typically present at about 5-20% by weight of the weight of component (A) in the composition.

According to a further aspect of the invention there is provided a composite comprising, or derivable from, the thermoset resin compositions and curable polymer compositions described hereinabove.

According to a further aspect of the invention there is provided a method for the manufacture of a composite comprising, or derivable from, the thermoset resin compositions and curable polymer compositions described hereinabove.

The compositions described herein are particularly suitable for fabrication of structures, including load-bearing or impact resisting structures. For this purpose, the compositions may contain a reinforcing agent such as fibres. Fibres can be added short or chopped typically of mean fibre length not more than 2 cm, for example about 6 mm. Alternatively, and preferably, the fibres are continuous and may, for example, be unidirectionally-disposed fibres or a woven fabric, i.e. the composite material comprises a prepreg. Combinations of both short and/or chopped fibres and continuous fibres may be utilised. The fibres may be sized or unsized. Fibres can be added typically at a concentration of 5 to 35, preferably at least 20%, by weight. For structural applications, it is preferred to use continuous fibre for example glass or carbon, especially at 30 to 70, more especially 50 to 70% by volume.

The fibre can be organic, especially of stiff polymers such as poly paraphenylene terephthalamide, or inorganic. Among inorganic fibres, glass fibres such as "E" or "S" can be used, or alumina, zirconia, silicon carbide, other compound ceramics or metals. A very suitable reinforcing fibre is carbon, especially as graphite. Graphite fibres which have been found to be especially useful in the invention are those supplied by Cytec under the trade designations T650-35, T650-42 and T300; those supplied by Toray under the trade designation T800-HB; and those supplied by Hexcel under the trade designations AS4, AU4, IM 8 and IM 7.

Organic or carbon fibre is preferably unsized or is sized with a material that is compatible with the composition according to the invention, in the sense of being soluble in the liquid precursor composition without adverse reaction or of bonding both to the fibre and to the thermoset/thermoplastic composition described herein. In particular, carbon or graphite fibres that are unsized or are sized with resin precursor or (poly)arylsulphone are preferred. Inorganic fibre preferably is sized with a material that bonds both to the fibre and to the polymer composition; examples are the organo-silane coupling agents applied to glass fibre.

The composition may further contain a relatively minor amount of conventional toughening agents, i.e. the component (C) defined hereinabove constitutes the major portion of the toughening agents present, and in one embodiment component (C) is the only toughening agent present. Conventional toughening agents include particulate toughening agents, for instance aggregates such as glass beads, rubber particles and rubber-coated glass beads, filler such as polytetrafluoroethylene, silica, graphite, boron nitride, mica, talc and vermiculite, pigments, nucleating agents, and stabilisers such as phosphates. Liquid rubbers having reactive groups may also be used. The total of such materials and any fibrous reinforcing agent in the composition is typically at least 20% by volume, as a percentage of the total volume of the poly(aryl)sulphone/thermoset mixture. The percentages of fibres and such other materials are calculated on the total composition after reaction or processing at the hereinbelow defined temperatures.

Preferably, the composites are obtained from a curable composition made by mixing the thermoset benzoxazine resin precursor, the arylsulphone-containing benzoxazine component, and optionally the polyarylsulphone, and (at some stage) any fibrous reinforcing agent and other materials. A solvent may be present to aid processing. The solvent and the proportion thereof are chosen so that the mixture of the components forms at least a stable emulsion, preferably a stable apparently single-phase solution. The ratio of solvent to the combination of component (C) and (where used) component (B) is suitably in the range 5:1 to 20:1 by weight. Preferably a mixture of solvents is used, for example of a halogenated hydrocarbon and an alcohol, in a ratio suitably in the range 99:1 to 85:15. Conveniently the solvents in such a mixture should boil at under 100° C. at 1 atm pressure and should be mutually miscible in the proportions used. Alternatively the components can be brought together by hot melting and/or high shear.

The mixture is stirred until sufficiently homogeneous. Thereafter any solvent is removed by evaporation to give a resin composition. Evaporation is suitably at 50-200° C. and, at least in its final stages, can be at subatmospheric pressure, for example in the range 13.33 Pa to 1333 Pa (0.1 to 10 mm Hg). The resin composition preferably contains up to 5% w/w of volatile solvent, to assist flow when used to impregnate fibres. This residual solvent will be removed in contact with the hot rollers of the impregnating machine.

Suitably the composition in the form of a resin solution is transferred onto a suitable mould or tool for preparation of a panel, prepreg or the like, the mould or tool having been preheated to a desired degassing temperature. The stable emulsion is combined with any reinforcing, toughening, filling, nucleating materials or agents or the like, and the temperature is raised to initiate curing thereof. Suitably curing is carried out at elevated temperature up to 200° C., preferably in the range of 160 to 200° C., more preferably at about 170-190° C., and with use of elevated pressure to restrain deforming effects of escaping gases, or to restrain void formation, suitably at pressure of up to 10 bar, preferably in the range of 3 to 7 bar abs. Suitably the cure temperature is attained by heating at up to 5° C./min. for example 2° C. to 3° C./min and is maintained for the required period of up to 9 hours, preferably up to 6 hours, for example 3 to 4 hours. Pressure is released throughout and temperature reduced by cooling at up to 5° C./min. for example up to 3° C./min. Post-curing at temperatures in the range of 190° C. to 200° C. may be performed, at atmospheric pressure, employing suitable heating rates to improve the glass transition temperature of the product or otherwise. The mould or tool may be constructed of any suitable material, for instance an unsaturated polyester or thermoset resin such as epoxy or bis-maleimides having a heat resistance in excess of the forming temperature to be employed. Reinforcement is suitably provided in the form of glass fibres. Composite moulds may be prepared in conventional manner for use according to the present invention.

The composition, possibly containing some volatile solvent already present or newly added, can be used for example as an adhesive or for coating surfaces or for making solid structures by casting possibly in a foamed state. Short fibre reinforcement may be incorporated with composition prior to curing thereof. Preferably a fibre-reinforced composition is made by passing essentially continuous fibre into contact with such resin composition. The resulting impregnated fibrous reinforcing agent may be used alone or together with other materials, for example a further quantity of the same or a different polymer or resin precursor or mixture, to form a shaped article. This technique is described in more detail in EP-A-56703, 102158 and 102159.

A further procedure comprises forming incompletely cured composition into film by, for example, compression moulding, extrusion, melt-casting or belt-casting, laminating such films to fibrous reinforcing agent in the form of, for example, a non-woven mat of relatively short fibres, a woven cloth or essentially continuous fibre in conditions of temperature and pressure sufficient to cause the mixture to flow and impregnate the fibres and curing the resulting laminate.

Plies of impregnated fibrous reinforcing agent, especially as made by the procedure of one or more of EP-A 56703, 102158, 102159, can be laminated together by heat and pressure, for example by autoclave, vacuum or compression moulding or by heated rollers, at a temperature above the curing temperature of the thermosetting resin or, if curing has already taken place, above the glass transition temperature of the mixture, conveniently at least 180° C. and typically up to 200° C., and at a pressure in particular in excess of 1 bar, preferably in the range of 1-10 bar.

The resulting multi-ply laminate may be anisotropic in which the fibres are continuous and unidirectional, orientated essentially parallel to one another, or quasi-isotropic in each ply of which the fibres are orientated at an angle, conveniently 45° as in most quasi-isotropic laminates but possibly for example 30° or 60° or 90° or intermediately, to those in the plies above and below. Orientations intermediate between anisotropic and quasi-isotropic, and combination laminates, may be used. Suitable laminates contain at least 4 preferably at least 8, plies. The number of plies is dependent on the application for the laminate, for example the strength required, and laminates containing 32 or even more, for example several hundred, plies may be desirable. There may be aggregates, as mentioned above in interlaminar regions. Woven fabrics are an example of quasi-isotropic or intermediate between anisotropic and quasi-isotropic.

The curable polymer composition is preferably adapted to be cured at a temperature of less than that at which the material constituting the mould or tool on or in which it is intended to cure the resin composition becomes heat sensitive in any way.

According to a further aspect of the invention, there is provided a method for the manufacture of a thermoset resin comprising disposing the composition in a suitable mould or tool, or equivalent state in which it is to be formed, subjecting the composition to the desired elevated temperature at suitable pressure, for example at atmospheric pressure, and maintaining the temperature for a required period, as hereinbefore defined.

According to a further aspect of the invention, there is provided a prepreg comprising a thermoset resin composition as hereinbefore defined and continuous fibres, particularly a prepreg obtained by a process as hereinbefore defined.

According to a further aspect of the invention, there is provided a composite comprising a pre-preg as hereinbefore defined. The composite may comprise pre-pregs laminated together by heat and pressure, for example by autoclave, compression moulding, or by heated rollers, at a temperature above the curing temperature of the polymer composition.

The present invention is applicable to the manufacture of composites by conventional prepreg technology and also by resin infusion technology (as described for instance in US-2004/0041128). Resin infusion is a generic term which covers processing techniques such as Resin Transfer Molding (RTM), Liquid Resin Infusion (LRI), Vacuum Assisted Resin Transfer Molding (VARTM), Resin Infusion with Flexible Tooling (RIFT), Vacuum Assisted Resin Infusion (VARI), Resin Film Infusion (RFI), Controlled Atmospheric Pressure Resin Infusion (CAPRI), VAP (Vacuum Assisted Process) and Single Line Injection (SLI). The composites described herein particularly include composites formed through the use of resin-soluble thermoplastic veils in a resin infusion process as described in US-2006/0252334, the disclosure of which is incorporated herein by reference. In one embodiment, the composite is manufactured through resin infusion wherein a support structure comprising structural reinforcement fibers (dry) and the resin-soluble thermoplastic veil element is placed into a bag, mold or tool to provide a perform, a curable resin matrix composition is injected/infused directly into the combined structural reinforcement fibers and veil, and then cured.

According to a further aspect of the invention, there is provided a thermoplast, or a thermoplast-modified, thermoset resin shaped product comprising or derived from a composition, pre-preg or composite as hereinbefore defined, particularly one which is obtained by a method as hereinbefore defined. Preferably such product is selected from components suitable for use in transport applications (including aerospace, aeronautical, nautical and land vehicles, and including the automotive, rail and coach industries), in building/construction applications or in other commercial applications.

According to a further aspect of the invention, there is provided a curable polymer composition, thermoset resin composition, composite or pre-preg as hereinbefore defined for use as a component in the aforementioned transport applications, or as a building/construction or other commercial product or component thereof.

According to a further aspect of the invention, there is provided a polyarylsulphone comprising ether-linked repeating units, optionally further comprising thioether-linked repeating units, the units being selected from:

and optionally from:

wherein:
Ar is phenylene;
n=1 to 2 and can be fractional;
a=1 to 3 and can be fractional and when a exceeds 1, said phenylene groups are linked linearly through a single chemical bond or a divalent group other than —SO$_2$—, or are fused together,
provided that the repeating unit —[ArSO$_2$Ar]$_n$— is always present in the polyarylsulphone in such a proportion that on average at least two of said —[ArSO$_2$Ar]$_n$— units are in sequence in each polymer chain present,
wherein the polyarylsulphone comprises one or more reactive pendant and/or end group(s) selected from benzoxazine, and wherein the number average molecular weight of the polyarylsulphone is in the range from about 2,000 to about 60,000, as described hereinabove.

According to a further aspect of the invention, there is provided an arylsulphone-containing benzoxazine compound of formula (II), as described hereinabove:

wherein $Z^2$ comprises one or more arylsulphone unit(s), —[Ar—$SO_2$—Ar]$_n$—, and optionally further comprises one or more arylene unit(s) —[Ar]$_a$—, wherein said arylsulphone unit(s) and arylene unit(s) are linked by ether linkages (—O—) and/or thio-ether linkages (—S—);

wherein Ar is phenylene;

n=1 to 2 and can be fractional;

a=1 to 3 and can be fractional and when a exceeds 1, said phenylene groups are linked linearly through a single chemical bond or a divalent group other than —$SO_2$—, or are fused together;

wherein $R^{10}$ and $R^{11}$ are independently selected from hydrogen, alkyl, cycloalkyl and aryl, and preferably $R^{10}$ and $R^{11}$ are independently selected from alkyl, cycloalkyl and aryl, wherein compounds in which $R^{10}$ and $R^{11}$ are hydrogen either comprise a plurality of —[Ar—$SO_2$—Ar]$_n$— units, or n is greater than 1, or comprise at least one thio-ether linkage, or comprise one or more —[Ar]$_a$— units wherein a is greater than 1, or comprise three or more —[Ar]$_a$— units, or comprise —[Ar]$_a$— units in which the phenylene groups are bound to adjacent groups in a meta-configuration, or a combination thereof, and wherein the number average molecular weight of the compound is less than 2000.

According to a further aspect of the invention, there is provided an arylsulphone-containing benzoxazine compound of formula (III), as described hereinabove:

(III)

and $Z^3$ is selected from the group consisting of $SO_2$ and $Z^2$, and in one embodiment from $Z^2$ alone;

wherein $Z^2$ comprises one or more arylsulphone unit(s), —[Ar—$SO_2$—Ar]$_n$—, and optionally further comprises one or more arylene unit(s) —[Ar]$_a$—, wherein said arylsulphone unit(s) and arylene unit(s) are linked by ether linkages (—O—) and/or thio-ether linkages (—S—);

wherein Ar is phenylene;

n=1 to 2 and can be fractional;

a=1 to 3 and can be fractional and when a exceeds 1, said phenylene groups are linked linearly through a single chemical bond or a divalent group other than —$SO_2$—, or are fused together;

wherein $R^{10}$ and $R^{11}$ are independently selected from H, alkyl, cycloalkyl and aryl, preferably wherein $R^{10}$ and $R^{11}$ are independently selected from H, alky and cycloalkyl, particularly when $Z^3$ is $SO_2$, and wherein the number average molecular weight of the compound is less than 2000.

The invention is now illustrated in non-limiting manner with reference to the following examples.

EXAMPLES

In the following examples, there are described synthetic procedures for preparing benzoxazines based on m-ESEDA, 3'3-DDS, having the structures below, and a PES:PEES copolymer as defined hereinabove.

The following test methods were used to characterise the examples:

(i) Glass transition temperature was assessed by dynamic mechanical thermal analysis (DMTA) using a Rheometric Scientific ARES machine at a heating rate of 3° C. min$^{-1}$ from 90° C. to 250° C. (frequency 0.1 Hz; strain 0.1%). Samples are cut using an Isomet 1000 diamond saw, to a width of 4-5 mm, a thickness 2.5-3.0 times smaller than the width, and to 40 mm in length.

(iii) Flexural modulus was assessed using ASTM D790.

(iv) The E-modulus, tensile strength ($K_{IC}$) and tear propagation ($G_{IC}$) of the samples were assessed using ISO test 13586-1: "Determination of fracture toughnes ($G_C$ and $K_C$)—Linear elastic fracture mechanics (LEFM) approach.", 2000.

Example 1: m-ESEDA Benzoxazine 86.40 g p-cresol, 48.00 g p-formaldehyde and 86.50 g m-ESEDA were added to a glass jar equipped with overhead stirrer. The initially solid blend was heated in an oil bath to 85° C. for 2 hours. The temperature was increased to 130° C. and held for a further 30 minutes. The crude melt was poured into 500 cm$^3$ diethyl ether and stirred for thirty minutes before being filtered and ground. It was then purified by Soxhlet extraction for six hours using diethyl ether solvent. After this time it was filtered and dried. The solid was washed in 250 cm$^3$ 0.1 mol dm$^{-3}$ NaOH solution at 70° C. in an oil bath for thirty minutes and filtered and dewatered. The solid was then washed in 400 cm$^3$ water using overhead stirring for 30 minutes, filter-dried, then water-washed twice and filter-dried again. The final product was left to dry at 20-30° C. in vacuo. This gave 115.68 g of a light brown solid (83% yield).

Example 2: 3',3-DDS Benzoxazine 108.00 g p-cresol, 60.00 g p-formaldehyde and 62.00 g 3',3-DDS were added to a glass jar equipped with overhead stirrer. The initially solid blend was heated in an oil bath to 85° C. for 2 hours. The temperature was increased to 130° C. and held for a further 30 minutes. The crude melt was poured into 600 cm$^3$ diethyl ether and stirred for thirty minutes before being filtered and ground. It was then purified by Soxhlet extraction for six hours using diethyl ether solvent. After this time it was filtered and dried. The solid was washed in 250 cm$^3$ 0.1 mol dm$^{-3}$ NaOH solution at 70° C. in an oil bath for thirty minutes and filtered and dewatered. The solid was then washed in 400 cm$^3$ water using overhead stirring for 30 minutes, filter-dried, then water-washed twice and filter-dried again. The final product was left to dry at 20-30° C. in vacuo. 105.07 g of a white solid was collected (82% yield).

Example 3: Benzoxazine-Terminated Polyarylsulphone 43.20 g p-cresol, 24.00 g p-formaldehyde and 86.04 g of an amine-terminated polyarylsulphone (a PES:PEES copolymer of molecular weight 9000-12000 of general formula (C) as defined herein) were added to a round bottomed flask equipped with overhead stirrer. The initially solid blend was heated in an oil bath to 85° C. for 2 hours. The crude melt was poured into 400 cm$^3$ water and stirred for thirty minutes before being filtered. The solid was cryofractured in a grinding-mill and then macerated in warm water. The powder was then filtered, dried, washed in 250 cm$^3$ 0.1 mol dm$^{-3}$ NaOH solution at 70° C. for thirty minutes and the product dewatered. The solid was re-ground and washed again in NaOH solution. Purification was by Soxhlet extraction for six hours using diethyl ether solvent and air dried. The solid was washed in 200 cm$^3$ 0.1 mol dm$^{-3}$ NaOH solution at 70° C. for thirty minutes then washed in 600 cm$^3$ water using overhead stirring for 30 minutes. The filtrate was dewatered, washed again in water and filtered. The final product was dried in vacuo at 20-30° C. 78.22 g of off white solid was collected (88% yield).

Example 4: 10% m-ESEDA Benzoxazine in Bisphenol-A Benzoxazine

The compound of Example 1 was used to prepare a curable polymer composition, as follows. 3 g m-ESEDA benzoxazine and 27 g bisphenol-A benzoxazine (Huntsman Advanced Materials) were weighed into a 125 cm$^3$ glass jar. The jar was then clamped into an oil bath set and equilibrated to 135° C. An overhead stirred was placed into the jar and stirring was commenced. As the powders in the jar melt the stirrer was placed deeper into the vessel and its speed was increased. Once effective stirring was achieved it was continued for 30 minutes. An aluminium mould was preheated to 100° C. and at the end of the 30 minutes stirring time the benzoxazine blend was poured into the mould. The resin was degassed at between 95-120° C. for 1-2 hours.

Figure 1:
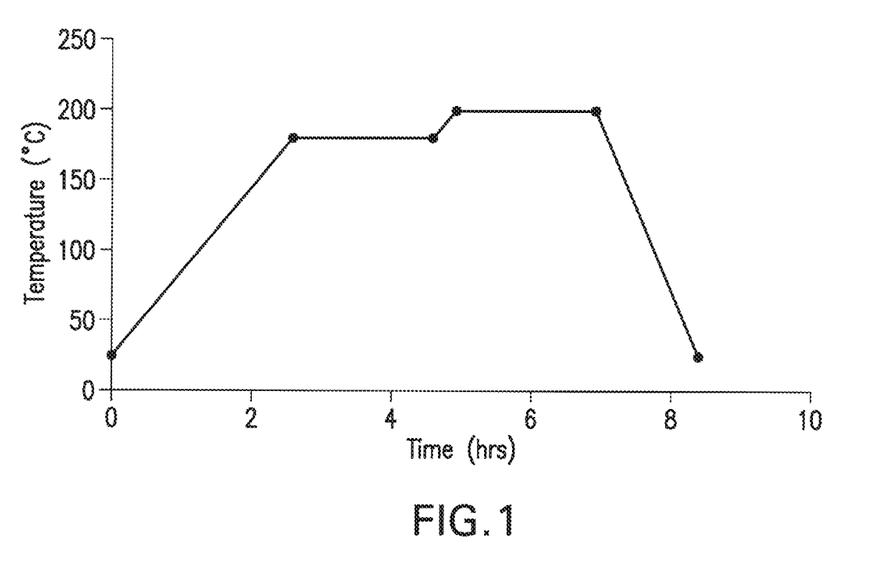
FIG. 1 illustrates a curing cycle for a polymer composition according to one example.

The composition was then cured according to the following cure cycle, which was used for all benzoxazine dishes and plaques described herein: 25° C.-180° C. at 1° C. min$^{-1}$, held for 2 hr, 180° C. to 200° C. at 1° C. min$^{-1}$, held for 2 hr, 200° C. to 25° C. at 2° C. min$^{-1}$. The cure cycle is illustrated in FIG. 1.

Control Example 1 and Examples 5 and 6

The procedure of Example 4 was repeated with various loadings (0%, 30% and 50%) of the m-ESEDA benzoxazine.

Control Example 2 and Examples 7, 8 and 9

The procedure of Control Example 1 and Examples 4, 5 and 6 were repeated with bisphenol-F benzoxazine (Huntsman Advanced Materials)

Examples 10 to 15

The procedure of Examples 4 to 9 were repeated for the 3',3-DDS benzoxazine, prepared as described above.

The miscibility of each of the bisphenol benzoxazines with either the m-ESEDA benzoxazine or the 3',3-DDS benzoxazine, at each of the concentrations noted above was assessed by visual inspection. Miscibility was generally excellent, and resulted in an essentially transparent cured neat resin plaque, containing a homogeneous single-phase composition.

Comparative Examples 1 and 2

Control Examples 1 and 2 were repeated except that an amine-terminated polyarylsulphone thermoplastic toughening agent (a PES:PEES copolymer of molecular weight 9000-12000 of general formula (C) as defined herein) was added to each of the bisphenol benzoxazines at a loading of 10% by weight. The components exhibited poor miscibility and the cured samples exhibited a two phase structure, a bisphenol-rich phase and a KM-polymer-rich phase. The KM polymer-rich phase exhibited a honeycomb-like structure which, without wishing to be limited by theory, is thought to arise by the KM polymer settling out during cure and becoming highly viscous, which in turn traps residual solvent or entrained air in the sample leading to a porous structure. Further, it is thought that the bisphenol-rich phase reduces in viscosity as the KM polymer settles and bubbles of solvent or air escape through this lower viscosity layer.

Examples 16 to 25

Comparative Examples 1 and 2 were repeated for each bisphenol benzoxazine, except that a proportion of the bisphenol benzoxazine precursor in the curable polymer composition was replaced by either the m-ESEDA benzoxazine or the 3',3-DDS benzoxazine. Miscibility improved with increasing levels of m-ESEDA benzoxazine or 3',3-DDS benzoxazine.

Figure 3:
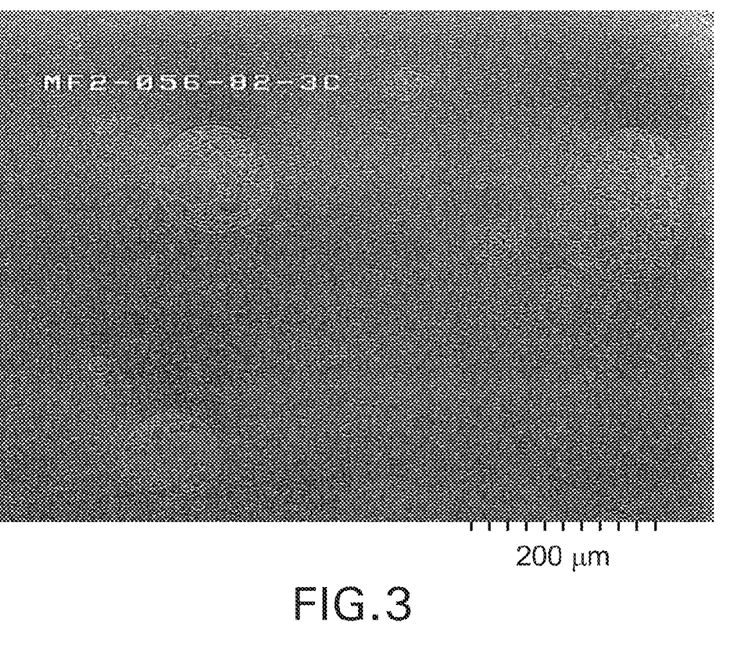
FIG. 3 is a Scanning Electron Microscope (SEM) image showing non-uniform particulate morphology of a thermoplastic toughening agent in a resin matrix.
Figure 4:
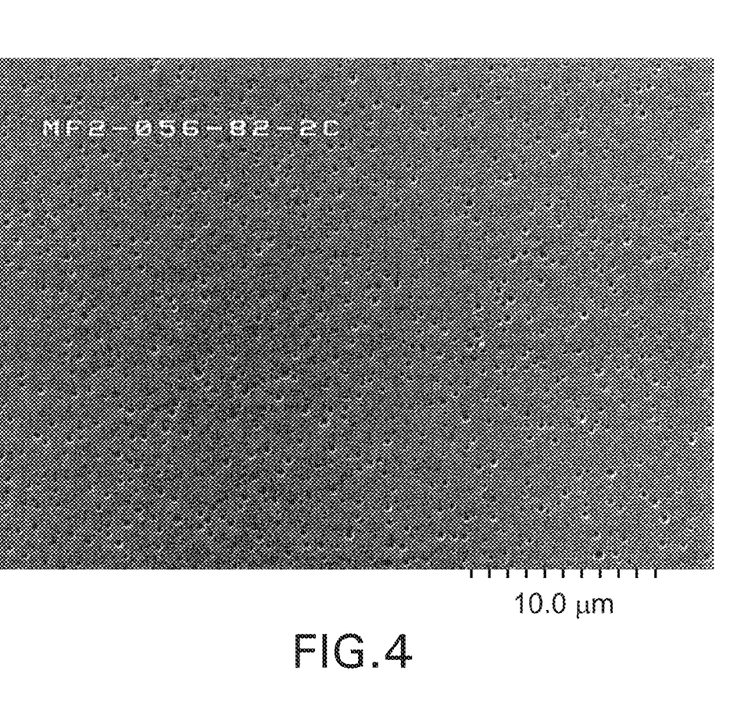
FIG. 4 is a SEM image showing fine particulate morphology of a thermoplastic toughening agent in a resin matrix.

Upon curing, the thermoplastic toughening agent becomes insoluble in the thermoset benzoxazine resin matrix and phase separation occurs. In the absence of compatabilisation between the thermoplastic toughener and the base resin, gross phase-separation occurs resulting in two distinct layers of material. In the compositions of the invention, the thermoplastic toughening agent remains as a discrete particulate phase dispersed within and throughout the thermoset resin matrix. Particulate phases may show phase inversion or additional particulate inclusions. The particulate phase may be classed as "non-uniform", in which the particulate phases are non-uniform in size and typically range from about 5 µm to about 300 µm, or as "fine particulate", in which the particulate phases are generally uniformly less than about 5 µm. The SEM micrographs of FIGS. 3 and 4 illustrate non-uniform particulate morphology, and fine particulate morphology, respectively. Fine particulate morphology is preferred.

The results of the above experiments are summarised in Tables 1 and 2 below.

TABLE 1

| Example | BOX$^a$ (wt %) | AS-BOX$^b$ (wt %) | PAS$^c$ (wt %) | Miscibility | Cured structure |
|---|---|---|---|---|---|
| Bisphenol-A benzoxazine and m-ESEDA benzoxazine | | | | | |
| Control 1 | 100 | 0 | — | n/a | Single phase |
| Ex. 4 | 90 | 10 | — | miscible | Single phase |
| Ex. 5 | 70 | 30 | — | miscible | Single phase |
| Ex. 6 | 50 | 50 | — | miscible | Single phase |

TABLE 1-continued

| Example | BOX[a] (wt %) | AS-BOX[b] (wt %) | PAS[c] (wt %) | Miscibility | Cured structure |
|---|---|---|---|---|---|
| Bisphenol-F benzoxazine and m-ESEDA benzoxazine | | | | | |
| Control 2 | 100 | 0 | — | n/a | Single phase |
| Ex. 7 | 90 | 10 | — | miscible | Single phase |
| Ex. 8 | 70 | 30 | — | miscible | Single phase |
| Ex. 9 | 50 | 50 | — | miscible | Single phase |
| Bisphenol-A benzoxazine and 3',3-DDS benzoxazine | | | | | |
| Ex. 10 | 90 | 10 | — | miscible | Single phase |
| Ex. 11 | 70 | 30 | — | miscible | Single phase |
| Ex. 12 | 50 | 50 | — | miscible | Single phase |
| Bisphenol-F benzoxazine and 3',3-DDS benzoxazine | | | | | |
| Ex. 13 | 90 | 10 | — | miscible | Single phase |
| Ex. 14 | 70 | 30 | — | miscible | Single phase |
| Ex. 15 | 50 | 50 | — | miscible | Single phase |

[a]BOX = bisphenol-A benzoxazine or bisphenol-F benzoxazine
[b]AS-BOX = arylsulphone benzoxazine (component (B))
[c]PAS = polyarylsulphone (component (C))

TABLE 2

| Ex. | BOX[a]:AS-BOX[b] ratio | BOX[a] + AS-BOX[b] total wt % | PAS[c] wt % | Miscibility | Cured structure |
|---|---|---|---|---|---|
| Bisphenol-A benzoxazine, m-ESEDA benzoxazine and PES:PEES polymer | | | | | |
| C. Ex. 1 | 100:0 | 90 | 10 | immiscible | Gross phase separation |
| Ex. 16 | 67:33 | 90 | 10 | miscible | Non uniform particulate |
| Ex. 17 | 44:56 | 90 | 10 | miscible | Predominantly fine particulate |
| Bisphenol-F benzoxazine, m-ESEDA benzoxazine and PES:PEES polymer | | | | | |
| C. Ex. 2 | 100:0 | 90 | 10 | immiscible | Gross phase separation |
| Ex. 18 | 89:11 | 90 | 10 | miscible | Non uniform particulate |
| Ex. 19 | 67:33 | 90 | 10 | miscible | Predominantly fine particulate |
| Ex. 20 | 44:56 | 90 | 10 | miscible | Fine particulate |
| Bisphenol-A benzoxazine, 3',3-DDS benzoxazine and PES:PEES polymer | | | | | |
| Ex. 21 | 67:33 | 90 | 10 | miscible | Fine particulate |
| Ex. 22 | 50:50 | 90 | 10 | miscible | Fine particulate |
| Bisphenol-F benzoxazine, 3',3-DDS benzoxazine and PES:PEES polymer | | | | | |
| Ex. 23 | 89:11 | 90 | 10 | miscible | Non uniform particulate |
| Ex. 24 | 67:33 | 90 | 10 | miscible | Fine particulate |
| Ex. 25 | 50:50 | 90 | 10 | miscible | Fine particulate |

[a]BOX = bisphenol-A benzoxazine or bisphenol-F benzoxazine
[b]AS-BOX = arylsulphone benzoxazine (component (B))
[c]PAS = polyarylsulphone (component (C))

Figure 2:
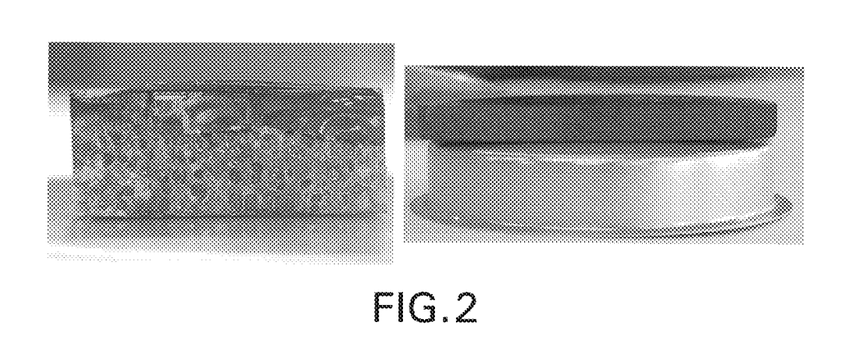
FIG. 2 are photographs of cured polymer samples for comparison.

From Table 1 and 2 it is apparent that the m-ESEDA and 3'3-DDS benzoxazines are miscible with the commercially available bisphenol-A and bisphenol-F benzoxazines, and that the polyarylsulphone toughening agent polymer is immiscible with both bisphenol benzoxazines unless 3'3-DDS or m-ESEDA benzoxazine is added as a compatabiliser. It is this compatibilisation of the resin to KM polymer which facilitates toughening of the cured material without gross phase-separation and without significant deterioration of other properties such as $T_g$ and modulus. FIG. 2 compares photographs of cured samples of comparative example 1 and example 16, showing the gross phase-separation of the comparative example.

The cured samples were also analysed by dynamic mechanical thermal analysis (DMTA) to determine the thermo-mechanical properties and by SEM to determine the morphology. Plaques of the cured samples were also analysed by linear elastic fracture mechanics (LEFM) and to determine flexural modulus. The glass-transition temperature of the cured resins, as measured by DMTA, are shown in Table 3 below. The results of the LEFM and flexural modulus analyses are also presented in Table 3 below.

The data in Table 3 demonstrate that the $T_g$ of the benzoxazine resin is not significantly affected by the addition of compatibilising and toughening agents, and indeed can be increased in some instances.

The data in Table 3 demonstrate the improved mechanical properties of the benzoxazine resin toughened by the thermoplastic KM polymer which has been compatibilised into the resin by m-ESEDA and 3'3-DDS benzoxazines, in terms of both improved tensile strength ($K_{1C}$) and improved tear propagation ($G_{1C}$). The data further demonstrate that this increased toughness is achieved without loss of modulus or $T_g$. Indeed, like Tg, the modulus can be increased in some instances. However, the data in Table 3 also demonstrate that there is an optimum concentration range for the compatibiliser, at least at the concentrations of thermoplastic toughening agent used in the examples.

TABLE 3

| Example | Composition | Tg (° C.) | $K_{1C}$ (MPa m$^{0.5}$) | $G_{1C}$ (J m$^{-2}$) | E-mod (GPa) | Flex-mod (GPa) |
|---|---|---|---|---|---|---|
| Control 1 | Bisphenol-A benzoxazine | 182 | 0.65 (0.06) | 128 (23) | 4.39 (0.22) | 5.17 |
| Ex. 4 | Bisphenol-A benzoxazine; 10% m-ESEDA benzoxazine | 186 | — | — | — | — |
| Ex. 5 | Bisphenol-A benzoxazine; 30% m-ESEDA benzoxazine | 193 | 0.62 (0.02) | 117 (9) | 4.61 (0.37) | — |
| Ex. 16 | Bisphenol-A benzoxazine; 30% m-ESEDA benzoxazine; 10% KM180 | 194 | 0.76 (0.06) | 176 (30) | 4.44 (0.25) | — |
| Ex. 17 | Bisphenol-A benzoxazine; 50% m-ESEDA benzoxazine; 10% KM180 | 202 | 0.63 (0.05) | 119 (20) | 3.94 (0.24) | — |
| Ex. 11 | Bisphenol-A benzoxazine; 30% 3,3'-DDS benzoxazine | 179 | — | — | — | 5.56 |
| Ex. 21 | Bisphenol-A benzoxazine; 30% 3,3'-DDS benzoxazine; 10% KM180 | 180 | 0.82 (0.05) | 202 (26) | 4.49 (0.23) | 5.29 |
| Ex. 22 | Bisphenol-A benzoxazine; 50% 3,3'-DDS benzoxazine; 10% KM180 | 176 | — | — | — | — |

The invention claimed is:

1. A curable polymer composition comprising:
   (A) a thermoset benzoxazine resin precursor component; and
   (C) a polyarylsulphone thermoplastic toughening agent component comprising benzoxazine pendant and/or end-groups.

2. A composition according to claim 1 wherein component (C) comprises benzoxazine-terminated polyarylsulphone compounds.

3. A composition according to claim 1 wherein said polyarylsulphone thermoplastic toughening agent component (C) is present at no more than about 50% by weight, relative to the total weight of components (A) and (C) in the composition.

4. A composition according to claim 1 wherein the component (A) comprises a compound of formula (I):

(I)

wherein:
$Z^1$ is selected from a direct bond, —$C(R^3)(R^4)$—, —$C(R^3)$(aryl)-, —C(O)—, —S—, —O—, —S(O)—, a divalent heterocycle and —$[C(R^3)(R^4)_x$-arylene-$[C(R^5)(R^6)]_y$—, or the two benzyl rings of the benzoxazine moieties may be fused;

$R^1$ and $R^2$ are independently selected from alkyl, cycloalkyl and aryl;

$R^3$, $R^4$, $R^5$ and $R^6$ are independently selected from H, $C_{1-8}$ alkyl, and halogenated alkyl; and x and y are independently 0 or 1.

5. A composition according to claim 1 further comprises one or more reactive diluents.

6. A composition according to claim 5, wherein said reactive diluents are thermoset polymer precursors selected from epoxy resins and phenolic resins, and said reactive diluents are present from about 20% to about 40% by weight of component (A) in the composition.

7. A composite comprising the composition of claim 1 and reinforcing fibres.

8. A composite according to claim 7, wherein said reinforcing fibres are made of a material selected from the group consisting of: glass, alumina, zirconia, silicon carbide, ceramics, metals, carbon, and poly paraphenylene terephthalamide.

* * * * *